United States Patent [19]

Christensen et al.

[11] 4,123,547

[45] Oct. 31, 1978

[54] THIENAMYCIN SULFOXIDE AND SULPHONE

[75] Inventors: Burton G. Christensen, Metuchen; Edward Walton, Scotch Plains, both of N.J.

[73] Assignee: Merck & Co., Inc., Rahway, N.J.

[21] Appl. No.: 833,620

[22] Filed: Sep. 15, 1977

Related U.S. Application Data

[63] Continuation-in-part of Ser. No. 821,679, Aug. 4, 1977, abandoned, which is a continuation of Ser. No. 667,323, Mar. 16, 1976, abandoned.

[51] Int. Cl.$^2$ .................. C07D 487/04; A61K 31/40
[52] U.S. Cl. ................... 424/274; 260/376.31
[58] Field of Search ............... 260/326.31; 424/274

[56] References Cited

U.S. PATENT DOCUMENTS

| | | | |
|---|---|---|---|
| 3,950,357 | 4/1976 | Kahan et al. | 260/326.31 |
| 4,000,129 | 10/1976 | Verwey | 260/239.1 |
| 4,022,773 | 5/1977 | Ishimaru | 260/239.1 |

OTHER PUBLICATIONS

Fieser et al.; Advanced Organic Chemistry, p. 313 (1961).

*Primary Examiner*—Donald G. Daus
*Assistant Examiner*—Mary C. Vaughn
*Attorney, Agent, or Firm*—Frank M. Mahon; James A. Arno; Julian S. Levitt

[57] ABSTRACT

Thienamycin sulfoxide (I, $n=1$), Thienamycin sulfone (I, $n=2$), and their pharmaceutically acceptable salts are disclosed to be useful as antibiotics:

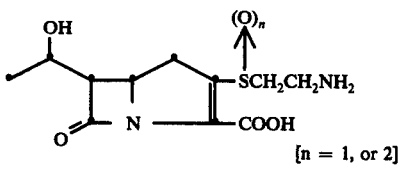

[$n = 1$, or 2]

Also disclosed are processes for the preparation of such compounds, pharmaceutical compositions comprising such compounds, and methods of treatment comprising administering such compounds and compositions when an antibiotic effect is indicated.

3 Claims, No Drawings

THIENAMYCIN SULFOXIDE AND SULPHONE

BACKGROUND OF THE INVENTION

This application is a continuation-in-part of U.S. patent application Ser. No. 821,679 filed Aug. 4, 1977, now abandoned which in turn is a continuation of U.S. pat. application Ser. No. 667,323 filed Mar. 16, 1976, now abandoned.

This invention relates to the novel antibiotics Thienamycin sulfoxide ($n=1$) and Thienamycin sulfone ($n=2$) which have the structure:

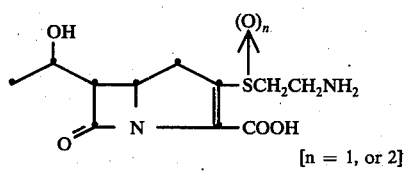

[n = 1, or 2]

This invention also relates to the pharmaceutically acceptable salts of I which are also useful as antibiotics. This invention also relates to processes for the preparation of such compounds, pharmaceutical compositions comprising such compounds and methods of treatment comprising administering such compounds and compositions when an antibiotic effect is indicated.

Thienamycin is disclosed and claimed in co-pending commonly assigned U.S. patent application Ser. No. 526,992 (filed Nov. 25, 1974) now U.S. Pat. No. 3,950,357 issued Apr. 13, 1976; said application is incorporated hereby by reference since Thienamycin may serve as the starting material in the preparation of the compounds of the present ivention. Thienamycin is known to have the following structural formula (II):

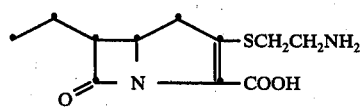

Thienamycin and all of its isomers (in pure form and as mixtures) are also obtainable by the total synthesis disclosed and claimed in co-pending, commonly assigned U.S. patent application Ser. No. 792,071 (28 Apr., 1977), now abandoned. This application is incorporated herein by reference to the extent that it makes available all isomers of II as starting materials in the preparation of the compounds of the present invention. Additionally incorporated by reference is co-pending commonly assigned U.S. patent application Ser. No. 734,584 (filed 10-21-76) which discloses and claims two distinct isomeric forms of II which are antibiotics and which are isolated, as N-acetyl derivatives, as natural products of fermentation.

There is a continuing need for new antibiotics. For unfortunately, there is no static effectiveness of a given antibiotic because continued wide scale usage of any such antibiotic selectively gives rise to resistant strains of pathogens. In addition, the known antibiotics suffer from the disadvantage of being effective only against certain types of microorganisms. Accordingly, the search for new antibiotics continues.

Unexpectedly, it has been found that the compounds of the present invention are broad spectrum antibiotics, which are useful in animal and human therapy and in inanimate systems.

Thus, it is an object of the present invention to provide a novel class of antibiotics which possess the basic nuclear structure, I, given above. These antibiotics are active against a broad range of pathogens which representatively include both gram positive bacteria such as *S. aureus, S. pyogenes* and *B. subtilis* and gram negative bacteria such as *E. coli, Proteus morganii* and *Klebsiella*. Further objects of this invention are to provide chemical processes for the preparation of such antibiotics and their non-toxic pharmaceutically acceptable salt derivatives; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention are conveniently prepared by mild oxidation of II or of a derivative of II according to the following reaction scheme:

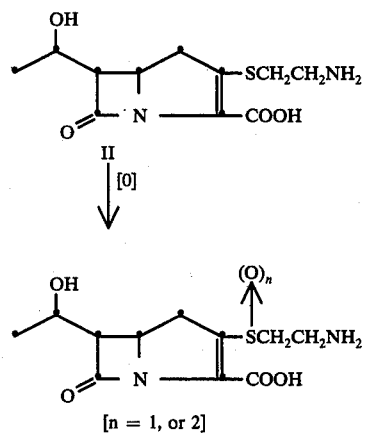

[n = 1, or 2]

Relative to the above reaction scheme, it is recognized that the sulfoxide ($n = 1$) is quantitively obtained when one equivalent of the oxidizing agent, [0], is taken; whereas two equivalents provides the sulphone embodiment ($n = 2$). There is no criticality as to the precise identity of the oxidizing agent. Suitable oxidizing agents include peracids such as m-chloroperbenzoic acid and peracetic acid; other representative oxidizing agents include potassium permanganate, hydrogen peroxide, and ozone, for example. There is no criticality as to reaction solvent — any solvent being acceptable which is inert or substantially inert during the course of reaction and which effectively solubilizes the thienamycin substrate. Representative examples of suitable solvents for the oxidation include tetrahydrofuran, methylenechloride, and water. Typically, the reaction is conducted at a temperature of from about 0° to about 50° C., for from a few minutes to about one hour for the sulfoxide and, for the sulfone, 1 to 6 hours.

The compounds of the present invention are valuable antibiotics which are active against various gram-positive and gram-negative bacteria and, accordingly, find utility in human and veterinary medicine and in inanimate systems. The compounds of this invention can therefore be used as antibacterial drugs for treating infections caused by gram-positive or gram-negative bacteria, for example against *Staphylococcus aureus, Escheria coli, Klebsiella pneumoniae, Bacillus subtilis, Salmonella typhosa, Pseudomonas* and *Bacterium proteus*.

The antibacterial compounds of the invention may further be utilized as additives to animal feedstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as the active ingredient in any one of a variety of pharmaceutical preparations. These antibiotics and their corresponding pharmaceutically acceptable salts, may be employed in capsule form or as tablets, powders, or liquid solutions or as suspensions or elixirs. They may be administered orally, intravenously or intramuscularly. Such pharmaceutically acceptable forms are prepared from procedures well-known in the art.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillters for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops. Topical applications may be formulated in hydrophobic or hydrophilic bases as ointments, creams, lotions, paints, or powders.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1 to about 99% of active material, the preferred range being from about 10–60%. The compositions will generally contain from about 15 mg. to about 1500 mg. of the active ingredient; however, in general, it is preferable to employ a dosage amount in the range of from about 250 mg. to 1000 mg. In parenteral administration the unit dosage is usually the pure compounds in a slightly acidified sterile water solution or as the form of a soluble powder intended for solution.

The following examples further illustrate, but do not limit the product, process, compositional or method of treatment aspects of the present invention.

EXAMPLE 1

Preparation of Thienamycin Sulfoxide

Step A: Preparation of O, N-bis Trimethylsilyl-Thienamycin trimethylsilyl ester, Th(TMS)₃

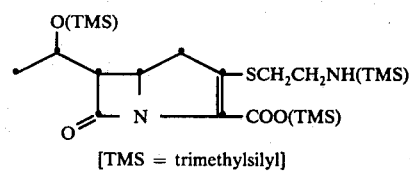

[TMS = trimethylsilyl]

Thienamycin (36.7 mg., 0.135 mmole) is suspended in 20 ml. tetrahydrofuran (THF) under a nitrogen atmosphere and is concentrated to 5 ml; hexamethyldisilazane (0.5 ml) and trimethylchlorosilazane (150 μl) is added. The mixture is reacted for 20 minutes at 25° C., with vigorous stirring. The suspension is then centrifuged to remove ammonium chloride. The supernatant is evaporated to an oil under a nitrogen stream to provide O, N-bis trimethylsilylthienamycin trimethylsilyl ester.

Step B: Preparation of Thienamycin sulfoxide

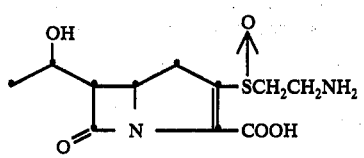

The Th(TMS)₃ from Step A is dissolved in 3 ml of tetrahydrofuran and treated with a solution of 23.4 mg of m-chloroperbenzoic acid in 1 ml. of tetrahydrofuran. The reaction solution is concentrated to dryness and the residue is dissolved in 5 ml of 0.1N pH 7.0 sodium phosphate buffer and kept at 5° C. for 24 hours to remove the trimethylsilyl blocking groups. The resulting solution comprising thienamycin sulfoxide and exhibiting an absorption maximum at 282 nm is evaporated to dryness to provide the desired product, thienamycin sulfoxide.

Following the procedure of Example 1 except that the two equivalents of m-chloroperbenzoic acid (46.8 mg) are employed, rather than the one equivalent of Example 1, thienamycin sulphone is obtained.

EXAMPLE 2

Preparation of Thienamycin Sulfoxide

A solution of 36.7 mg (0.135 mmole) of thienamycin in 2 ml of water is cooled to 5° C and treated with a solution of 26.2 mg of the sodium salt of m-chloroperbenzoic acid and the mixture is stirred until the oxidant is consumed. (negative test with KI-starch test paper). The reaction mixture is acidified to pH 3 with dilute hydrochloric acid and extracted with three 4 ml portions of ether to remove the m-chloroperbenzoic acid. The aqueous phase is neutralized to pH 7 with dilute sodium hydroxide. The salts are removed from the aqueous phase by passing it through a column of 50 ml of XAD resin and eluting with distilled water. The fractions containing the thienamycin sulfoxide are pooled and freeze-dried to give a residue of thienamycin sulfoxide.

Similarly, when any isomeric form of II or mixture of isomers of II is substituted, in equivalent amount, for the thienamycin of Examples 1 and 2, there is obtained the corresponding antibiotic sulfoxide or sulphone of II.

EXAMPLE 3

Preparation of Thienamycin Sulfoxide

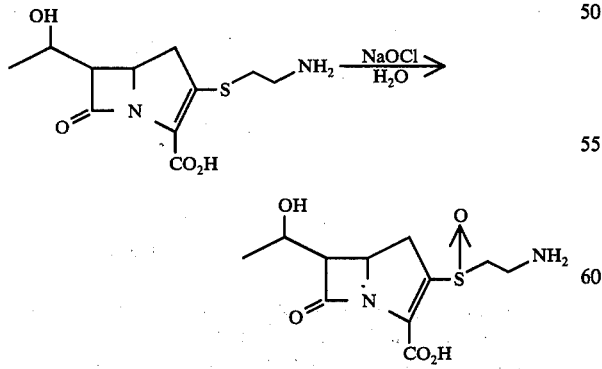

Aqueous sodium hypochlorite (0.75 ml of a 5.25% solution) is added dropwise over 45 sec. to a stirred solution of thienamycin (92.5 mg) in water (75 ml) at 25° C. The pH climbs from 5.2 to 10.0. After 1 min, the pH is adjusted to 7.0 with 0.1N hydrochloric acid (0.33 ml); UV analysis of the reaction mixture shows that 75% of the original UV absorption is retained. Electrophoresis (20 min, 2KV, pH 7) shows a continuous bioactive streak from the origin to +5 cm (monoanion range). The reaction mixture is concentrated in vacuo at 25° C to 1.5 ml and charged onto a Dowex 50 column (100 ml, sodium form). The column is eluted with water while monitoring the effluent by UV and refractive index (RI). After the first RI (colored) band is rejected, the product is collected as a second RI colorless band. The product solutions gives a UV maximum at 289 nm, an origin bioactive spot by electrophoresis, and two close eluting bands in 3:1 ratio by HPLC, both more polar than thienamycin. Lyophilization of this solution provides an amorphous powder (33 mg) whose NMR spectrum is in accord with thienamycin sulfoxide.

EXAMPLE 4

Preparation of Thienamycin Sulfoxide

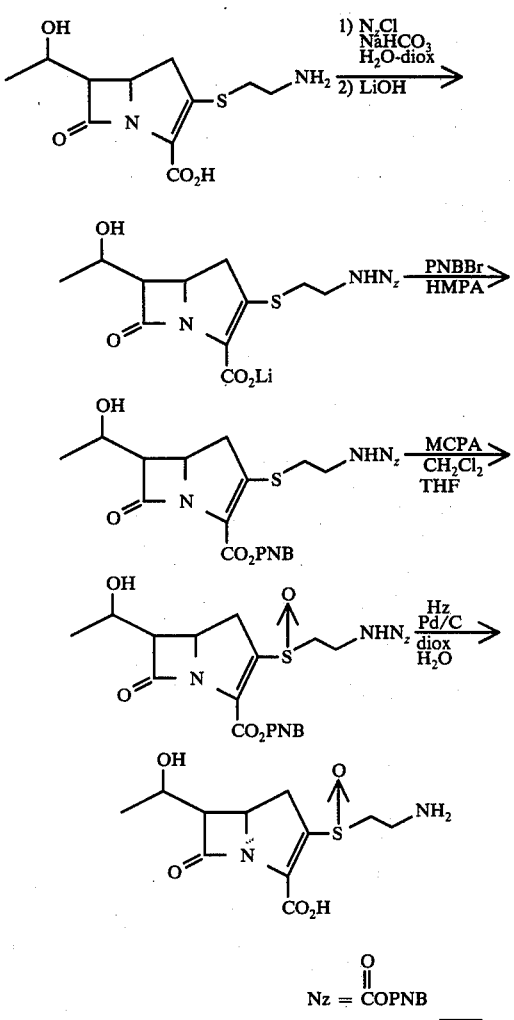

STEP A: N-(p-nitrobenzyloxycarbonyl)thienamycin p-nitrobenzyl ester

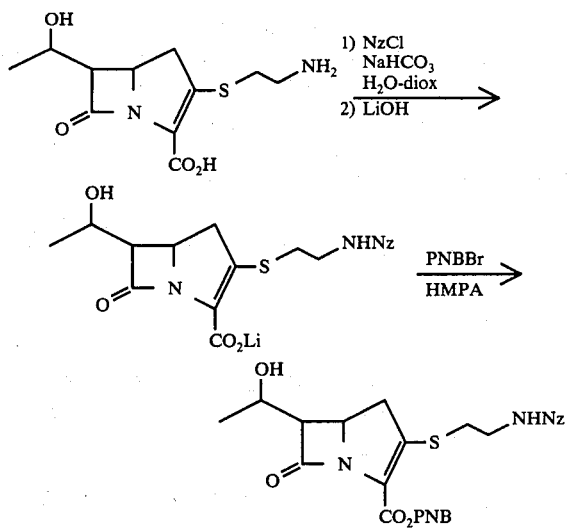

Thienamycin (140 mg, 0.51 mmol) is dissolved in ice-cold $H_2O$ (35 ml) and the solution is treated with $NaHCO_3$ (428 mg, 5.1 mmol). Dioxane (35 ml) is then added with stirring and ice-bath cooling. After 3 mins, a solution of p-nitrobenzyl chloroformate (165 mg, 0.765 mmol) in dioxane (2 ml) is added dropwise over 2 mins. The resulting mixture is stirred in the cold for 10 mins and then extracted with ice-cold $Et_2O$ (2×20 ml). The aqueous phase is separated, layered with ice-cold EtOAc (35 ml), and acidified to pH 2.3 with 1M $H_2SO_4$ while vigorously stirring in an ice-bath. The layers are separated and the aqueous portion extracted with more cold EtOAc (2×5 ml). The combined EtOAc extracts are washed with ice-cold brine and then extracted thoroughly with 0.05N aq. LiOH (10 ml). The LiOH extract is rotary evaporated to remove EtOAc and then lyophilized to provide crude N-(p-nitrobenzyloxycarbonyl)thienamycin lithium salt (288 mg) as a yellow solid.

A portion of the crude lithium carboxylate (250 mg) and p-nitrobenzyl bromide (373 mg, 1.73 mmol) in anhydrous HMPA (2.65 ml) are stirred at room temperature (25° C) for 105 mins. The mixture is diluted with EtOAc (60 ml), washed with $H_2O$ (2×50 ml), 5% $NaHCO_3$ (25 ml), $H_2O$ (2×25 ml), and brine (25 ml), dried with $MgSO_4$, filtered, and evaporated in vacuo (i.v.) to a yellow solid (423 mg). This material is triturated with $Et_2O$ to remove excess p-nitrobenzyl bromide and the remaining crystals are filtered off and dried i.v. to yield N-(p-nitrobenzyloxycarbonyl)thienamycin p-nitrobenzyl ester (126 mg) as a yellow solid: mp 163.5-165°; ir (Nujol mull) 1773 and 1690 cm$^{-1}$; nmr (DMSO—d$_6$) δ 1.15(d,3, $CH_3$), 2.8-3.6(m,7,$CH_2$, $SCH_2$, $NCH_2$, $H_6$), 4.0 (m,2,H5,H8), 5.22 (s,2, $NCO_2CH_2Ar$), 5.40(ABq, 2, $CO_2CH_2Ar$), 7.70(m,ArH), and 8.27(m,ArH). [Relative to the above text, $Et_2O$ symbolizes diethylether and EtOAc is ethylacetate.]

STEP B: Preparation of N-(p-nitrobenzyloxycarbonyl)thienamycin p-nitrobenzyl ester S-oxide

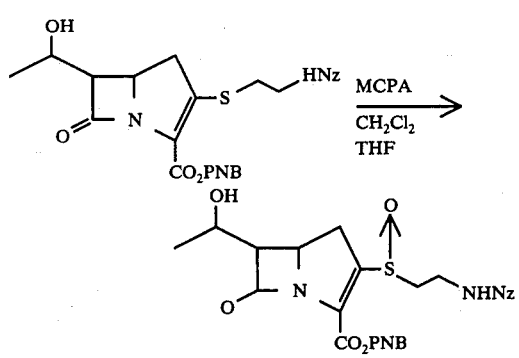

N-(p-nitrobenzyloxycarbonyl) thienamycin p-nitrobenzyl ester (117.3 mg, 0.20 mmol) is dissolved in anhydrous tetrahydrofuran (6.0 ml) and the solution is stirred under a nitrogen atmosphere with ice-bath cooling. A solution of 85% m-chloroperbenzoic acid (44.7 mg, 0.22 mmol) in anhydrous methylene chloride (2.0 ml) is added dropwise over 8 mins to the solution. The resulting solution is stirred in the cold an additional 12 mins, then diluted with ethyl acetate (20 ml), washed with 5% sodium bicarbonate (2 × 10 ml) and brine, dried with magnesium sulfate, filtered, and concentrated under reduced pressure to provide the crude sulfoxide (125 mg) as a pale yellow solid. The crude product is triturated with ethyl acetate (2 × 2 ml) and ethyl ether (2 × 4 ml) and dried in vacuo to yield substantially pure N-(p-nitrobenzyloxycarbonyl) thienamycin p-nitrobenzyl ester S-oxide (57 mg) as an off-white powder: mp 142°-143°; ir (nujol) 3450, 3315, 1780, 1695, 1520, and 1347 cm$^{-1}$; uv (dioxane) 266 (ε 21,200) and 325 (sh, ε 6150); nmr (CDCl$_3$, 300 MHz)δ 1.36 (d, $CH_3$), 3.23 (m, $SCH_2$), 3.32 (m, $CH_2$), 3.42 (dd, H$_6$), 3.78(m, $NCH_2$), 4.30(m, H8), 4.41(dt, H5), 5.24(ABq, $NCO_2CH_2Ar$), 5.39(ABq, $CO_2CH_2Ar$), 7.55(d, 2, ArH), 7.68(d, 2, ArH), 8.25(d, 2, ArH) and 8.28 (d, 2, ArH).

STEP C: Preparation of Thienamycin S-oxide

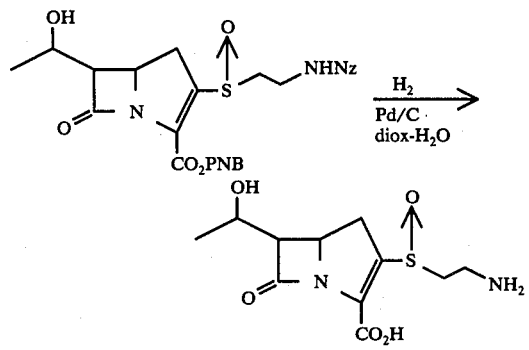

N-(p-nitrobenzyloxycarbonyl)thienamycin p-nitrobenzyl ester s-oxide (25 mg) is dissolved in dioxane (3.0 ml) and the solution is treated with 10% palladium on powdered charcoal (25 mg), ethanol (0.25 ml), 1M dipotassium hydrogen phosphate (0.05 ml), and deionized water (1.75 ml). The resulting mixture is hydrogenated on a Parr shaker for 1 hr. The pressure drops from 50 psi to 45 psi during the course of the reduction. The catalyst is removed by centrifugation and washed with 0.1M pH 7 phosphate buffer (1 ml) and water (1 ml). The combined superantants are washed with ethyl acetate (3 × 3 ml), concentrated in vacuo to 1 ml, and charged onto a Dowex 50-X4 column (1.4 × 20 cm, sodium form). The column is eluted with deionized water; 5.5 ml fractions being collected every 4.0 mins. The progress of the chromatograph is monitored by UV and HPLC. Fractions 5 and 6 are combined to give 11 ml of a solution containing thienamycin S-oxide. An aliquot (0.2 ml) of this solution diluted to 2.0 ml with water gives a UV spectrum having A=0.63 at 289 nm. The combined fractions 5–6 are brought to pH 6.8 with 1N hydrochloric acid, concentrated in vacuo to 3 ml, and lyophilized to afford thienamycin S-oxide as a light brown, amorphous powder: ir(nujol) 1765 cm$^{-1}$; UV(-H$_2$O) 289 nm; nmr(D$_2$O, 300 MHz) $\delta$ 1.29(d, 3, CH$_3$), 3.24 and 3.26 (d of ABq, CH$_2$), 3.5 (m, SCH$_2$ and NCH$_2$), 3.67(d of d,H6), 4.28(d of q, H8) and 4.42(d of t, H5).

EXAMPLE 5

Preparation of Pharmceutical Compositions

One such unit dosage form consists in mixing 120 mg. of thienamycin sulfoxide with 20 mg of lactose and 5 mg of magnesium stearate and placing the 145 mg mixture into a No. 3 gelatin capsule. Similarly, by employing more active ingredient and less lactose, other dosage forms can be put up in No 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
|---|---|
| Thienamycin Sulfoxide | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with a 15% cornstarch paste (6 mg.) and rough-screened. It is dried at 45° C., and screened again through No. 16 screens. The balance of the cornstarch and the magnesium stearate is added and the mixture is compressed into tablets, approximately 0.5 inch in diameter each weighing 800 mg.

| PARENTERAL SOLUTION | | |
|---|---|---|
| Ampoule: | | |
| Thienamycin sulfoxide | | 500 mg. |
| Diluent: Sterile Water for Injection | | 2 cc. |
| OPTHALMIC SOLUTION | | |
| Thienamycin sulfoxide | | 100 mg. |
| Hydroxypropylmethyl Cellulose | | 5 mg. |
| Sterile Water | to | 1 ml. |
| OTIC SOLUTION | | |
| Thienamycin Sulfoxide | | 100 mg. |
| Benzalkonium Chloride | | 0.1 mg. |
| Sterile Water | to | 1 ml. |
| TOPICAL OINTMENT | | |
| Thienamycin sulfoxide | | 100 mg. |
| Polyethylene Glycol 4000 U.S.P. | | 400 mg. |
| Polyethylene Glycol 400 U.S.P. | | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structural formula:

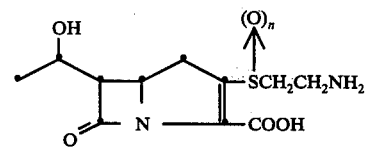

wherein $n$ is an integer selected from 1 or 2 and the non-toxic, pharmaceutically acceptable salts thereof.

2. The compound according to claim 1 wherein $n = 1$.

3. An antibacterial pharmaceutical composition comprising, in unitary dosage form, a therapeutically effective amount of a compound according to claim 1 and a pharmaceutical carrier therefor.

* * * * *